US011306080B2

(12) United States Patent
Artino et al.

(10) Patent No.: US 11,306,080 B2
(45) Date of Patent: Apr. 19, 2022

(54) CRYSTALLINE FORM OF A BACE INHIBITOR, COMPOSITIONS, AND USE

(71) Applicants:Merck Sharp & Dohme Corp., Rahway, NJ (US); Laura M. Artino, Oakhurst, NJ (US); William Morris, Randolph, NJ (US); Eric Sirota, Hoboken, NJ (US); Richard J. Varsolona, Scotch Plains, NJ (US)

(72) Inventors: Laura M. Artino, Oakhurst, NJ (US); William Morris, Randolph, NJ (US); Eric Sirota, Hoboken, NJ (US); Richard J. Varsolona, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 60 days.

(21) Appl. No.: 16/622,323

(22) PCT Filed: Jun. 8, 2018

(86) PCT No.: PCT/US2018/036572
§ 371 (c)(1),
(2) Date: Dec. 13, 2019

(87) PCT Pub. No.: WO2018/231634
PCT Pub. Date: Dec. 20, 2018

(65) Prior Publication Data
US 2020/0199117 A1    Jun. 25, 2020

Related U.S. Application Data

(60) Provisional application No. 62/524,843, filed on Jun. 26, 2017, provisional application No. 62/518,951, filed on Jun. 13, 2017.

(51) Int. Cl.
*C07D 417/12* (2006.01)

(52) U.S. Cl.
CPC ........ *C07D 417/12* (2013.01); *C07B 2200/13* (2013.01)

(58) Field of Classification Search
CPC .................................................... C07D 417/12
USPC ...................................................... 514/222.5
See application file for complete search history.

(56) References Cited

U.S. PATENT DOCUMENTS

| 8,729,071 B2 | 5/2014 | Scott et al. |
| 10,017,505 B2 | 7/2018 | Trzaska et al. |
| 10,035,796 B2 | 7/2018 | Kazakevich et al. |

FOREIGN PATENT DOCUMENTS

| WO | 2016025359 A1 | 2/2016 |
| WO | 2016025364 A1 | 2/2016 |
| WO | 2016053767 A1 | 4/2016 |
| WO | 2017083216 A1 | 5/2017 |

*Primary Examiner* — Kahsay Habte
(74) *Attorney, Agent, or Firm* — Jeffrey P. Bergman; Catherine D. Fitch

(57) ABSTRACT

The present invention provides a novel crystalline form of verubecestat (Crystalline Form II of Verubecestat) and pharmaceutically acceptable compositions thereof, each of which may be useful in treating, preventing, ameliorating, and/or delaying the onset of an Aβ pathology and/or a symptom or symptoms thereof. Non-limiting examples of such Aβ pathologies, including Alzheimer's disease and mild cognitive impairment, are disclosed herein.

21 Claims, 5 Drawing Sheets

CRYSTALLINE FORM OF A BACE INHIBITOR, COMPOSITIONS, AND USE

FIELD OF THE INVENTION

This invention provides a novel crystalline form of verubecestat (described below), a potent inhibitor of BACE-1 and BACE-2, pharmaceutically acceptable compositions thereof, and methods for their preparation and use in treating, preventing, ameliorating, and/or delaying the onset of an Aβ pathology and/or a symptom or symptoms thereof, such as Alzheimer's disease and mild cognitive impairment.

BACKGROUND

Amyloid beta peptide ("Aβ") is a primary component of β amyloid fibrils and plaques, which are regarded as having a role in an increasing number of pathologies. Examples of such pathologies include, but are not limited to, Alzheimer's disease, Down's syndrome, Parkinson's disease, memory loss (including memory loss associated with Alzheimer's disease and Parkinson's disease), attention deficit symptoms (including attention deficit symptoms associated with Alzheimer's disease ("AD"), Parkinson's disease, and Down's syndrome), dementia (including pre-senile dementia, senile dementia, dementia associated with Alzheimer's disease, Parkinson's disease, and Down's syndrome), progressive supranuclear palsy, cortical basal degeneration, neurodegeneration, olfactory impairment (including olfactory impairment associated with Alzheimer's disease, Parkinson's disease, and Down's syndrome), β-amyloid angiopathy (including cerebral amyloid angiopathy), hereditary cerebral hemorrhage, amnestic mild cognitive impairment ("MCI"), glaucoma, amyloidosis, type II diabetes, hemodialysis (β2 microglobulins and complications arising therefrom), neurodegenerative diseases such as scrapie, bovine spongiform encephalitis, Creutzfeld-Jakob disease, traumatic brain injury and the like.

Aβ peptides are short peptides which are made from the proteolytic break-down of the transmembrane protein called amyloid precursor protein ("APP"). Aβ peptides are made from the cleavage of APP by β-secretase activity at a position near the N-terminus of Aβ, and by gamma-secretase activity at a position near the C-terminus of Aβ. (APP is also cleaved by α-secretase activity, resulting in the secreted, non-amyloidogenic fragment known as soluble APPα.) Beta site APP Cleaving Enzyme-1 ("BACE-1") is regarded as the primary aspartyl protease responsible for the production of Aβ by β-secretase activity. The inhibition of BACE-1 has been shown to inhibit the production of Aβ.

AD is estimated to afflict more than 20 million people worldwide and is believed to be the most common cause of dementia. AD is a disease characterized by degeneration and loss of neurons and also by the formation of senile plaques and neurofibrillary tangles. Presently, treatment of Alzheimer's disease is limited to the treatment of its symptoms rather than the underlying causes. Symptom-improving agents approved for this purpose include, for example, N-methyl-D-aspartate receptor antagonists such as memantine (Namenda®, Forest Pharmaceuticals, Inc.), cholinesterase inhibitors such as donepezil (Aricept®, Pfizer), rivastigmine (Exelon®, Novartis), galantamine (Razadyne Reminyl®), and tacrine (Cognex®).

In AD, Aβ peptides, formed through β-secretase and gamma-secretase activity, can form tertiary structures that aggregate to form amyloid fibrils. Aβ peptides have also been shown to form Aβ oligomers (sometimes referred to as "Aβ aggregates" or "Abeta oligomers"). Aβ oligomers are small multimeric structures composed of 2 to 12 Aβ peptides that are structurally distinct from Aβ fibrils. Amyloid fibrils can deposit outside neurons in dense formations known as senile plaques, neuritic plaques, or diffuse plaques in regions of the brain important to memory and cognition. Aβ oligomers are cytotoxic when injected in the brains of rats or in cell culture. This Aβ plaque formation and deposition and/or Aβ oligomer formation, and the resultant neuronal death and cognitive impairment, are among the hallmarks of AD pathophysiology. Other hallmarks of AD pathophysiology include intracellular neurofibrillary tangles comprised of abnormally phosphorylated tau protein, and neuroinflammation.

Evidence suggests that Aβ, Aβ fibrils, aggregates, oligomers, and/or plaque play a causal role in AD pathophysiology. (Ohno et al., Neurobiology of Disease, No. 26 (2007), 134-145). Mutations in the genes for APP and presenilins 1/2 (PS1/2) are known to cause familial AD and an increase in the production of the 42-amino acid form of Aβ is regarded as causative. Aβ has been shown to be neurotoxic in culture and in vivo. For example, when injected into the brains of aged primates, fibrillar Aβ causes neuronal cell death around the injection site. Other direct and circumstantial evidence of the role of Aβ in Alzheimer etiology has also been published.

BACE-1 has become an accepted therapeutic target for the treatment of Alzheimer's disease, including prodromal treatment. For example, McConlogue et al., J. Bio. Chem., Vol. 282, No. 36 (September 2007), have shown that partial reductions of BACE-1 enzyme activity and concomitant reductions of Aβ levels lead to a dramatic inhibition of AO-driven AD-like pathology, making β-secretase a target for therapeutic intervention in AD. Ohno et al. Neurobiology of Disease, No. 26 (2007), 134-145, report that genetic deletion of BACE-1 in 5XFAD mice abrogates Aβ generation, blocks amyloid deposition, prevents neuron loss found in the cerebral cortex and subiculum (brain regions manifesting the most severe amyloidosis in 5XFAD mice), and rescues memory deficits in 5XFAD mice. The group also reports that Aβ is ultimately responsible for neuron death in AD and concludes that BACE-1 inhibition has been validated as an approach for the treatment of AD. Roberds et al., Human Mol. Genetics, 2001, Vol. 10, No. 12, 1317-1324, established that inhibition or loss of β-secretase activity produces no profound phenotypic defects while inducing a concomitant reduction in Aβ. Luo et al., Nature Neuroscience, Vol. 4, No. 3, March 2001, report that mice deficient in BACE-1 have normal phenotype and abolished β-amyloid generation.

More recently, Jonsson, et al. have reported in Nature, Vol. 488, pp. 96-99 (August 2012), that a coding mutation (A673T) in aPP gene protects against Alzheimer's disease and cognitive decline in the elderly without Alzheimer's disease. More specifically, an allele of rs63750847, a single nucleotide polymorphism (SNP), results in an alanine to threonine substitution at position 673 in APP (A673T). This SNP was found to be significantly more common in a healthy elderly control group than in an Alzheimer's disease group. A673T substitution is adjacent to aspartyl protease beta-site in APP, and results in an approximately 40% reduction in the formation of amyloidogenic peptides in a heterologous cell expression system in vitro. Jonsson, et al. report that an APP-derived peptide substrate containing a673T mutation is processed 50% less efficiently by purified human BACE-1 enzyme when compared to a wild-type peptide. Jonsson et al. indicate that the strong protective effect of aPP-A673T substitution against Alzheimer's disease provides proof of principle for the hypothesis that reducing the beta-cleavage of APP may protect against the disease.

BACE-1 has also been identified or implicated as a therapeutic target for a number of other diverse pathologies in which Aβ or Aβ fragments have been identified to play a causative role. One such example is in the treatment of AD-type symptoms of patients with Down's syndrome. The gene encoding APP is found on chromosome 21, which is also the chromosome found as an extra copy in Down's syndrome. Down's syndrome patients tend to acquire AD at an early age, with almost all those over 40 years of age showing Alzheimer's-type pathology. This is thought to be due to the extra copy of aPP gene found in these patients, which leads to overexpression of APP and therefore to increased levels of Aβ causing the prevalence of AD seen in this population. Furthermore, Down's patients who have a duplication of a small region of chromosome 21 that does not include aPP gene do not develop AD pathology. Thus, it is thought that inhibitors of BACE-1 could be useful in reducing Alzheimer's type pathology in Down's syndrome patients.

Another example is in the treatment of glaucoma (Guo et al., PNAS, Vol. 104, No. 33, Aug. 14, 2007). Glaucoma is a retinal disease of the eye and a major cause of irreversible blindness worldwide. Guo et al. report that Aβ colocalizes with apoptotic retinal ganglion cells (RGCs) in experimental glaucoma and induces significant RGC cell loss in vivo in a dose- and time-dependent manner. The group report having demonstrated that targeting different components of aβ formation and aggregation pathway, including inhibition of β-secretase alone and together with other approaches, can effectively reduce glaucomatous RGC apoptosis in vivo. Thus, the reduction of Aβ production by the inhibition of BACE-1 could be useful, alone or in combination with other approaches, for the treatment of glaucoma.

Another example is in the treatment of olfactory impairment. Getchell et al., Neurobiology of Aging, 24 (2003), 663-673, have observed that the olfactory epithelium, a neuroepithelium that lines the posterior-dorsal region of the nasal cavity, exhibits many of the same pathological changes found in the brains of AD patients, including deposits of Aβ, the presence of hyperphosphorylated tau protein, and dystrophic neurites among others. Other evidence in this connection has been reported by Bacon A W, et al., Ann NY Acad Sci 2002; 855:723-31; Crino P B, Martin J A, Hill W D, et al., Ann Otol Rhinol Laryngol, 1995; 104:655-61; Davies D C, et al., Neurobiol Aging, 1993; 14:353-7; Devanand D P, et al., Am J Psychiatr, 2000; 157:1399-405; and Doty R L, et al., Brain Res Bull, 1987; 18:597-600. It is reasonable to suggest that addressing such changes by reduction of Aβ by inhibition of BACE-1 could help to restore olfactory sensitivity in patients with AD.

For compounds which are inhibitors of BACE-2, another example is in the treatment of type-II diabetes, including diabetes associated with amyloidogenesis. BACE-2 is expressed in the pancreas. BACE-2 immunoreactivity has been reported in secretory granules of beta cells, co-stored with insulin and IAPP, but lacking in the other endocrine and exocrine cell types. Stoffel et al., WO2010/063718, disclose the use of BACE-2 inhibitors in the treatment of metabolic diseases such as Type-II diabetes. The presence of BACE-2 in secretory granules of beta cells suggests that it may play a role in diabetes-associated amyloidogenesis. (Finzi, G. Franzi, et al., Ultrastruct Pathol. 2008 November-December; 32(6):246-51.)

Other diverse pathologies characterized by the formation and deposition of Aβ or fragments thereof, and/or by the presence of amyloid fibrils, oligomers, and/or plaques, include neurodegenerative diseases such as scrapie, bovine spongiform encephalitis, traumatic brain injury ("TBI"), Creutzfeld-Jakob disease and the like, type II diabetes (which is characterized by the localized accumulation of cytotoxic amyloid fibrils in the insulin producing cells of the pancreas), and amyloid angiopathy. In this regard reference can be made to the patent literature. For example, Kong et al., US2008/0015180, disclose methods and compositions for treating amyloidosis with agents that inhibit Aβ peptide formation. As another example, Loane, et al. report the targeting of amyloid precursor protein secretases as therapeutic targets for traumatic brain injury. (Loane et al., "Amyloid precursor protein secretases as therapeutic targets for traumatic brain injury", Nature Medicine, Advance Online Publication, published online Mar. 15, 2009.) Still other diverse pathologies characterized by the inappropriate formation and deposition of Aβ or fragments thereof, and/or by the presence of amyloid fibrils, and/or for which inhibitor(s) of BACE are expected to be of therapeutic value are discussed further hereinbelow.

The compound:

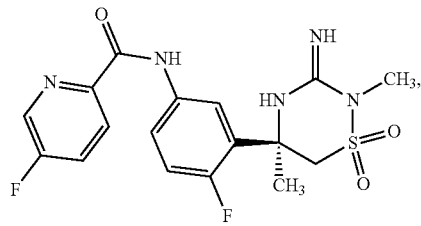 [SMILES: CN1C(=N)N[C@](C)(c2cc(NC(=O)c3ccc(F)cn3)ccc2F)CS1(=O)=O]

and its tautomer:

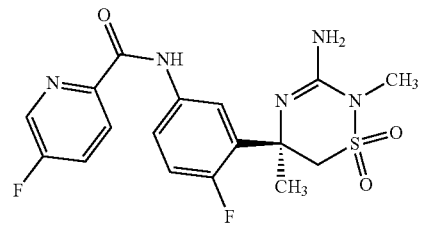 [SMILES: CN1C(N)=N[C@](C)(c2cc(NC(=O)c3ccc(F)cn3)ccc2F)CS1(=O)=O]

which are collectively and individually referred to herein as "verubecestat", and pharmaceutically acceptable salts thereof, are disclosed in PCT Patent Publication No. WO2011/044181 (incorporated herein by reference), as a potent inhibitor of BACE-1 and BACE-2, together with pharmaceutical compositions thereof. Also disclosed is the use of verubecestat in treating, preventing, ameliorating, and/or delaying the onset of an Aβ pathology and/or a symptom or symptoms thereof, including Alzheimer's disease. A preparation of verubecestat is also disclosed therein.

The "endo" (or "amino") tautomer of verubecestat may be depicted as

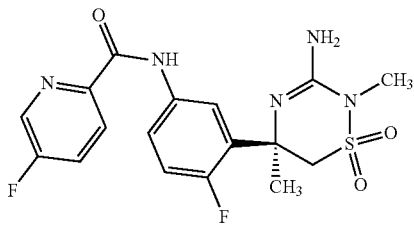 [SMILES: CN1C(N)=N[C@](C)(c2cc(NC(=O)c3ccc(F)cn3)ccc2F)CS1(=O)=O]

and named as N-[3-[(5R)-3-amino-5,6-dihydro-2,5-dimethyl-1,1-dioxido-2H-1,2,4-thiadiazin-5-yl]-4-fluorophenyl]-5-fluoro-2-pyridinecarboxamide.

The "exo" (or "imine") tautomer of verubecestat, which is also shown above, may be depicted as

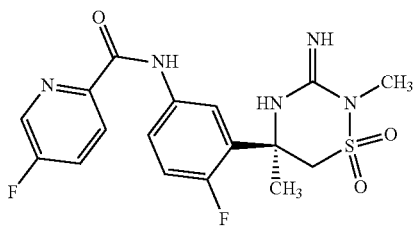 [SMILES: CN1C(=N)N[C@](C)(c2cc(NC(=O)c3ccc(F)cn3)ccc2F)CS1(=O)=O]

and named as 5-fluoro-N-[4-fluoro-3-[(5R)-tetrahydro-3-imino-2,5-dimethyl-1,1-dioxido-2H-1,2,4-thiadiazin-5-yl]phenyl]-2-pyridinecarboxamide.

For ease of description, and unless otherwise specified, the structural formula:

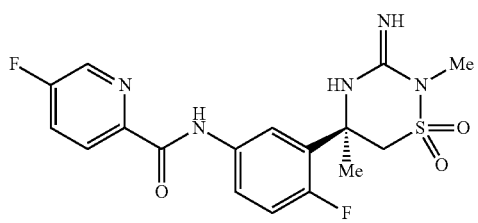 [SMILES: CN1C(=N)N[C@](C)(c2cc(NC(=O)c3ccc(F)cn3)ccc2F)CS1(=O)=O]

is intended to encompass the endo form, or the exo form, or a mixture of both of the endo and exo forms.

The physical and biological attributes of a drug's active ingredient, such as solubility, stability, melting point, bioavailability, and the like can be affected by the solid-state form. PCT publication numbers WO2016/025364 and WO2016053767 disclose certain forms of verubecestat. The present invention provides a novel crystalline form of verubecestat described herein, which, surprisingly and advantageously exhibits improved thermodynamic stability while maintaining good chemical stability and other advantageous properties, as described herein.

SUMMARY OF THE INVENTION

In one embodiment, the present invention provides a novel crystalline form of verubecestat, here referred to as "Crystalline Form II of Verubecestat" (or alternatively as "Crystalline Form II of verubecestat," or alternatively as "Cyrstalline Form II of Verubecestat", or alternatively as "Cyrstalline Form II", or as "Form II"). In other embodiments, the present invention provides pharmaceutically acceptable compositions of Crystalline Form II of Verubecestat. In further embodiments, the present invention provides methods for the use of the Crystalline Form II of Verubecestat in the preparation of a medicament which may be useful (alone or together with additional active ingredients) in treating, preventing, ameliorating, and/or delaying the onset of an Aβ pathology and/or a symptom or symptoms thereof. Non-limiting examples of such Aβ pathologies, including Alzheimer's disease and amnestic mild cognitive impairment, are disclosed herein.

DETAILED DESCRIPTION OF THE INVENTION

Definitions

Figure 1:
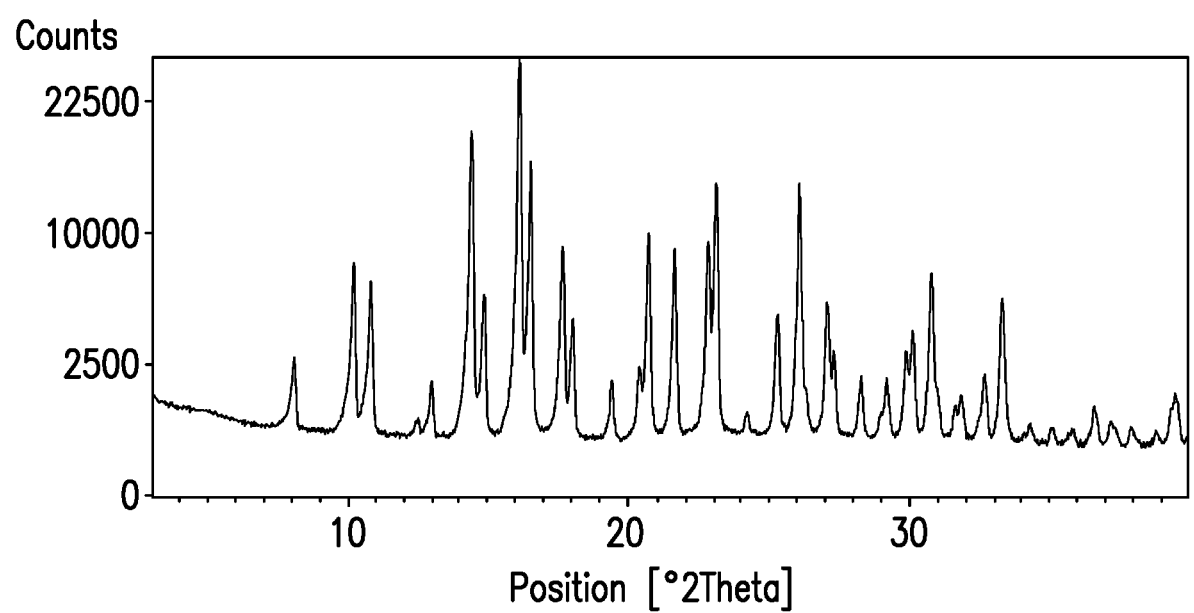
FIG. 1 is a graph of a Powder X-Ray Diffraction ("PXRD") pattern of Crystalline Form II of Verubecestat, generated using the equipment and methods described herein. The graph plots the intensity of the peaks as defined by counts per second versus the diffraction angle 2 theta (2Θ) in degrees.

The terms used herein have their ordinary meaning and the meaning of such terms is independent at each occurrence thereof. That notwithstanding and except where stated otherwise, the following definitions apply throughout the specification and claims.

"FIG" (or "FIG." or "Fig." or "Fig" or "fig." or "fig") means "Figure" (or "figure") and refers to the corresponding drawing.

"Patient" includes both human and other animals.

"Mammal" includes humans and other mammalian animals.

"m/z" refers to a mass spectrum peak.

"PXRD" refers to powder x-ray diffraction.

"DSC" refers to differential scanning calorimetry.

"TGA" refers to thermal gravimetric analysis.

"Excipient" means an essentially inert substance used as a diluent or to give form or consistency to a formulation.

The term "composition" (or "pharmaceutical composition" or "pharmaceutically acceptable composition") as used herein is intended to encompass a product comprising the specified ingredients in the specified amounts, as well as any product which results, directly or indirectly, from combining the specified ingredients in the specified amounts. The term is intended to encompass a product comprising active ingredient(s), and the inert ingredient(s), if any, that make up the carrier, as well as any product which results, directly or indirectly, from combination, complexation, or aggregation of any two or more of the ingredients, or from dissociation of one or more of the ingredients, or from other types of reactions or interactions of one or more of the ingredients. Accordingly, the pharmaceutical compositions of the invention encompass any composition made by admixing the Crystalline Form II of Verubecestat and a pharmaceutically acceptable carrier. By "pharmaceutically acceptable" it is meant the carrier, diluent or excipient must be compatible with the other ingredients of the formulation and not deleterious to the recipient thereof.

The term "composition" (or "pharmaceutical composition" or "pharmaceutically acceptable composition") as used herein is also intended to encompass either the bulk composition and/or individual dosage units. (Such compositions and units can additionally comprise additional active ingredients as described herein.) The bulk composition and each individual dosage unit can contain fixed amounts of active agent(s). The bulk composition is material that has not yet been formed into individual dosage units. Non-limiting examples of dosage units include oral dosage units such as tablets, pills and the like. Similarly, the herein-described method of treating a patient by administering a pharmaceutical composition of the present invention is also intended to encompass administration of afore-said bulk composition and individual dosage units.

As noted above, verubecestat is capable of tautomerism and may therefore be depicted as the "endo" (or "amine") form or the "exo" (or "imine") form, each of which are shown above. Those skilled in the art will appreciate that the relative amount(s) of each tautomeric form of verubecestat that is (or is not) present in a given sample may vary as influenced by the physical conditions in which the compound is present. As noted below, the endo (or amino) form of verubecestat has been observed to be the dominant tautomeric form in Crystalline Form II of Verubecestat. Thus, while the term "verubecestat" generally refers to each, and both, tautomeric forms, individually and together, all references to the various characterizations of Crystalline Form II of Verubecestat in each of the aspects and embodiments described herein include reference to the endo (amino) tautomeric form.

Synthesis of Verubecestat

A synthesis for the preparation of verubecestat is disclosed in WO2011/044181. Another synthesis is described in Applicant's PCT publication No. WO2016/025359, published Feb. 18, 2016, entitled "Process for the Preparation for a BACE inhibitor". Other syntheses are described in Applicant's PCT publication nos. WO2016025364 and WO2016053767. Additionally, a synthesis of verubecestat may be described according to General Scheme A and by the description that follows. Reactants for which a synthesis is not described are available commercially for purchase or within the level of the ordinarily skilled synthetic chemist.

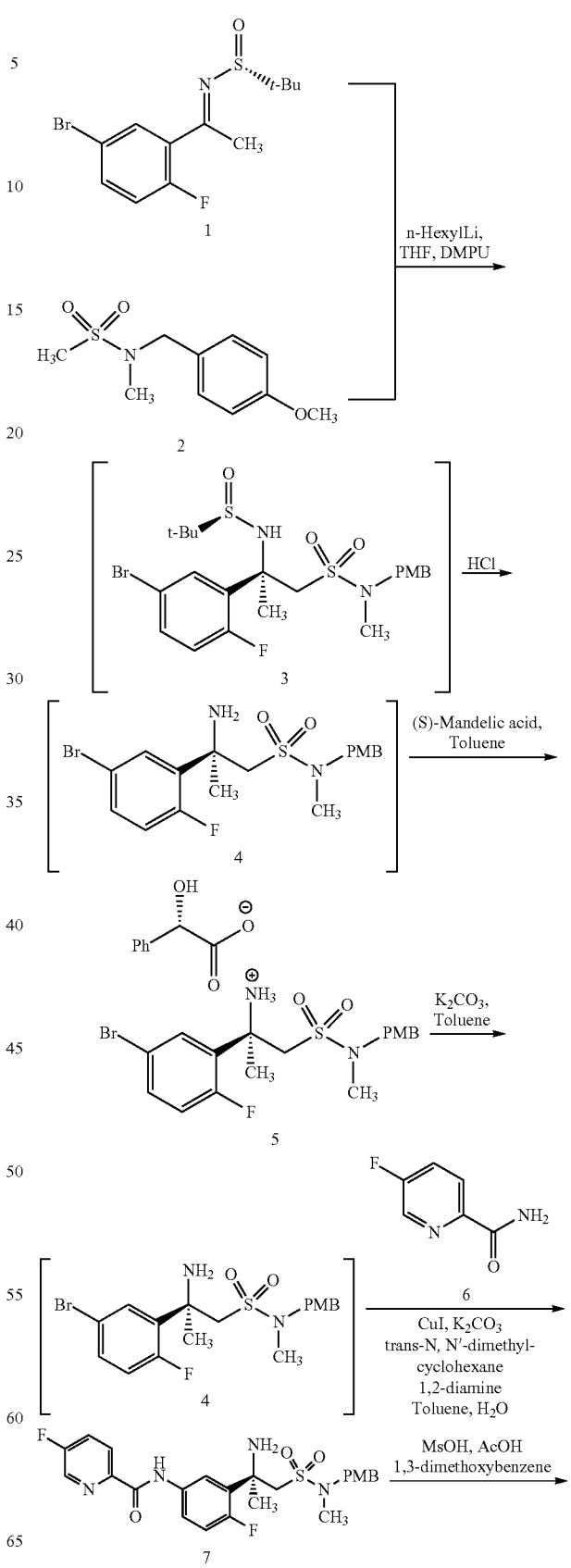

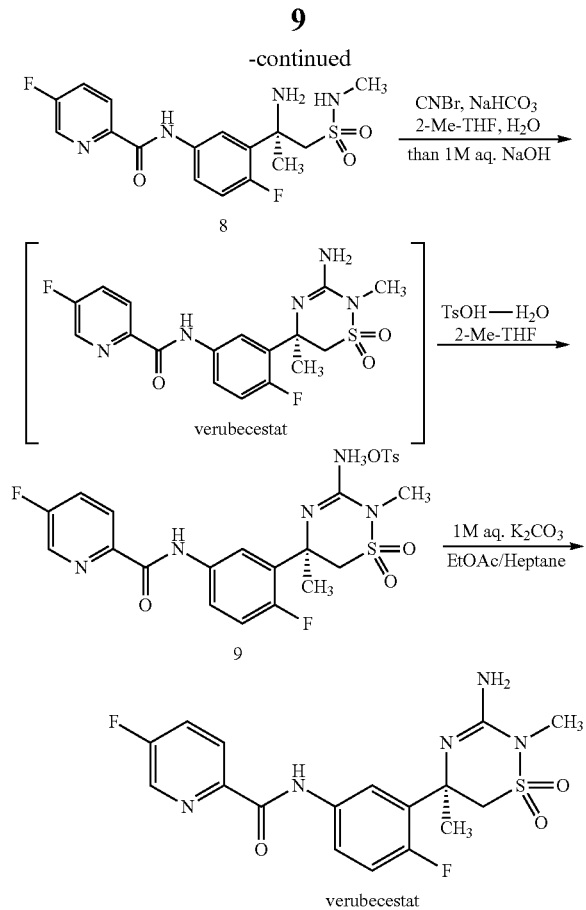

Sulfonamide 2 was treated with n-hexyllithium in the presence of 1,3-dimethyl-3,4,5,6-tetrahydro-2(1H)-pyrimidinone (DMPU) then condensed with ketamine 1 to form the non-isolated intermediate 3. This intermediate was treated with hydrochloric acid to form the amine 4 and then subsequently isolated as the (S)-mandelate salt 5. Mandelate salt 5 was free-based before undergoing coupling to 5-fluoropicolinamide 6 to afford C—N coupled intermediate 7. The para-methoxybenzyl (PMB) group was removed under acidic conditions to yield intermediate 8. Intermediate 8 was alkylated with cyanogen bromide (CNBr) before undergoing intramolecular cyclization to yield verubecestat which was initially isolated as the tosylate salt (9).

Crystalline Form II of Verubecestat

As noted above, the present invention provides a novel crystalline form of verubecestat as an anhydrous free base, herein referred to as "Crystalline Form II of verubecestat" (or alternatively as "Crystalline Form II" or "crystalline form II" or "Form II" or "form II").

Crystalline Form II of Verubecestat was prepared according to the procedure described below. As those skilled in the art will appreciate, the use of seed crystal in the preparation described below is not initially required but is used for optimal production after initial quantities of Crystalline Form II are produced. For the preparation of Crystalline Form II, suitable starting quantities of verubecestat, e.g., in the form of the tosylate salt of verubecestat, may be obtained from any suitable synthesis including those referenced and described above.

Preparation of the Crystalline Form II of Verubecestat

To a reactor (R1) equipped with a temperature probe, nitrogen inlet, and agitator was charged EtOAc (19.6 L) followed by the tosylate salt of verubecestat (1.96 kg) obtained as described in Scheme A above. Agitation of R1 was begun and the reaction mixture kept at 15-25° C. To R1 was charged 1 M aqueous K$_2$CO$_3$ (4.05 L) and the mixture agitated before the layers were allowed to settle and the bottom aqueous layer was removed; this process was repeated. Water (5.88 L) was then charged to R1 and the mixture agitated before the layers were allowed to settle and the bottom aqueous layer was removed, resulting in verubecestat in the organic layer. The temperature of R1 was adjusted to less than 35° C. and the batch was concentrated to 10.3 liters (L). Ethyl acetate (17.6 L) was added to R1 and the batch was again concentrated to 10.3 L.

The reactor (R1) was heated to 68° C. to 72° C. and the mixture was agitated for 30 minutes. The temperature was adjusted to 45° C. to 55° C. and n-heptane (0.43 L) was charged. Form 2 seeds (0.06 kg) were added to R1. The batch was allowed to age for 2 hours. n-Heptane (13.7 L) was then charged to R1 over 10 hours. The temperature was adjusted to 15° C. to 25° C. The solids were collected and washed with Ethyl Acetate/n-heptane (40/60 v/v, 5.88 L) and then heptane (5.88 L). The crystals were dried to provide Crystalline Form II of Verubecestat (1.27 kg).

In the procedure described above, the presence of certain impurities (even if present in otherwise acceptably small amounts) in the tosylate salt of verubecestat obtained in accordance with Scheme A above can kinetically impede the formation of Crystalline Form II of Verubecestat. For example, referring to Scheme A above, the conversion of intermediate 8 to verubecestat can result in the production of small amounts of (R)—N-(3-(3-cyanamido-2,5-dimethyl-1,1-dioxido-5,6-dihydro-2H-1,2,4-thiadiazin-5-yl)-4-fluorophenyl)-5-fluoropicolinamide that remain after the isolation of tosylate salt 9. Thus, strict regulation of the amount of CNBr can minimize the formation of such impurities and improve the rate of production of Crystalline Form II of Verubecestat.

Alternatively, Form II of Verubecestat can be prepared by conversion of a slurry of Crystalline Anhydrous Form 1 of Verubecestat (obtained as described in WO2016/025364) to Crystalline Form II of Verubecestat at a pH at or above 7.8, preferably between 7.8 and 10, more preferably at pH 10. Thus, in one example, Crystalline Form 2 of Verubecestat was prepared by adding 100 mg of Crystalline Anhydrous Form 1 of Verubecestat obtained as described in WO2016/025364 to 10 ml of 0.05M phosphate buffer solution at pH of 7.8 to a vial. In another example, Crystalline Form 2 of Verubecestat was prepared by adding 100 mg of Crystalline Anhydrous Form 1 of Verubecestat obtained as described in WO2016/025364 to 10 ml of Fisher blue buffer solution at pH of 10.00 to a vial. The slurry of Form 1 and buffer in each example was mixed at ambient temperature for 24 hours and filtered. The resulting solid in each example was confirmed by PXRD to be Crystalline Form 2 of Verubecestat.

Physical Characterization of the Crystalline Form II of Verubecestat

Powder X-ray diffraction (PXRD) pattern studies, differential scanning calorimeter (DSC) studies, thermogravimetric analysis (TGA), solid state NMR, and/or single crystal diffractometry are widely used to characterize molecular structures, crystallinity, and polymorphism and were used where indicated to characterize Crystalline Form II of Verubecestat. Those skilled in the art will appreciate that a crystalline form of a substance can be further characterized by combinations of measured PXRD values, DSC values, NMR, TGA, and/or crystal structure measurements. Thus, in another aspect, Crystalline Form II of Verubecestat is characterized by any combination of each of the aspects described herein.

Powder X-Ray Diffraction (PXRD)

Crystalline Form II of Verubecestat obtained as described above was subjected to PXRD analysis. Powder X-ray diffraction (PXRD) patterns were generated on a Philips Analytical X'Pert PRO X-ray Diffraction System™ with PW3040/60 console. A PW3373/00 ceramic Cu LEF X-ray tube K-Alpha radiation was used as the source. Data were acquired between 2° and 40° 2 theta with a step size of 0.02 degrees over step durations of 46 seconds. Samples were prepared on a zero background silicon holder. Those skilled in the art will recognize that the measurements of the PXRD peak locations for a given crystalline form of the same compound will vary within a margin of error. The margin of error for the 2-theta values measured as described herein is typically +/−0.2° 2-theta. Variability can depend on such factors as the system, methodology, sample, and conditions used for measurement. As will also be appreciated by the skilled crystallographer, the intensities of the various peaks reported in the figures herein may vary due to a number of factors such as orientation effects of crystals in the x-ray beam, the purity of the material being analyzed, and/or the degree of crystallinity of the sample. The skilled crystallographer also will appreciate that measurements using a different wavelength will result in different shifts according to the Bragg-Brentano equation. Such further PXRD patterns generated by use of alternative wavelengths are considered to be alternative representations of the PXRD patterns of the crystalline material of the present invention and as such are within the scope of the present invention.

A PXRD pattern of Crystalline Form II of Verubecestat generated using the equipment and procedures described above is displayed in FIG. 1. The intensity of the peaks (y-axis is in counts per second) is plotted versus the 2 theta angle (x-axis is in degrees 2 theta). In addition, the data were plotted with detector counts normalized for the collection time per step versus the 2 theta angle. Peak locations (on the 2 theta x-axis) consistent with these profiles are displayed in Table 1, (+/−0.2° 2 theta). The locations of these PXRD peaks are characteristic of the Crystalline Form II of Verubecestat.

TABLE 1

| Peak Location (degrees 2 theta (+/−0.2° 2 theta)) | d-spacing [Å] |
| --- | --- |
| 2.15 | 41.07 |
| 8.20 | 10.79 |
| 10.32 | 8.57 |
| 10.94 | 8.09 |
| 12.63 | 7.01 |
| 13.11 | 6.75 |
| 14.53 | 6.10 |
| 14.98 | 5.92 |
| 16.23 | 5.46 |
| 16.63 | 5.33 |
| 17.77 | 4.99 |
| 18.14 | 4.89 |
| 19.53 | 4.55 |
| 20.51 | 4.33 |
| 20.84 | 4.26 |
| 21.77 | 4.08 |
| 22.94 | 3.88 |
| 23.24 | 3.83 |
| 24.35 | 3.66 |
| 25.41 | 3.51 |
| 26.18 | 3.40 |

TABLE 1-continued

| Peak Location (degrees 2 theta (+/−0.2° 2 theta)) | d-spacing [Å] |
| --- | --- |
| 26.47 | 3.37 |
| 27.19 | 3.28 |
| 27.41 | 3.25 |
| 28.39 | 3.14 |
| 29.31 | 3.05 |
| 29.98 | 2.98 |
| 30.22 | 2.96 |
| 30.88 | 2.90 |
| 31.13 | 2.87 |
| 31.71 | 2.82 |
| 31.94 | 2.80 |
| 32.78 | 2.73 |
| 33.39 | 2.68 |
| 34.43 | 2.61 |
| 35.20 | 2.55 |
| 35.94 | 2.50 |
| 36.69 | 2.45 |
| 37.24 | 2.41 |
| 38.00 | 2.37 |
| 38.90 | 2.32 |
| 39.43 | 2.28 |
| 39.61 | 2.28 |

Thus, in one aspect, Crystalline Form II of Verubecestat is characterized by a powder x-ray diffraction pattern having each of the peak locations listed in Table 1, +/−0.2° 2-theta.

In another aspect, Crystalline Form II of Verubecestat is characterized by a powder x-ray diffraction pattern comprising two or more of the 2-theta values listed in Table 1, +/−0.2° 2-theta.

In another aspect, Crystalline Form II of Verubecestat is characterized by a powder x-ray diffraction pattern comprising three or more of the 2-theta values listed in Table 1, +/−0.2° 2-theta.

In another aspect, Crystalline Form II of Verubecestat is characterized by a powder x-ray diffraction pattern comprising four or more of the 2-theta values listed in Table 1, +/−0.2° 2-theta.

In another aspect, Crystalline Form II of Verubecestat is characterized by a powder x-ray diffraction pattern comprising six or more of the 2-theta values listed in Table 1, +/−0.2° 2-theta.

In another aspect, Crystalline Form II of Verubecestat is characterized by a powder x-ray diffraction pattern comprising nine or more of the 2-theta values listed in Table 1, +/−0.2° 2-theta.

In another aspect, Crystalline Form II of Verubecestat is characterized by a powder x-ray diffraction pattern comprising twelve or more of the 2-theta values listed in Table 1, +/−0.2° 2-theta.

In another aspect, Crystalline Form II of Verubecestat is characterized by the powder x-ray diffraction pattern substantially as shown in FIG. 1.

In a further aspect, the PXRD peak locations displayed in Table 1 and/or in FIG. 1 most characteristic of Crystalline Form II of Verubecestat can be selected and grouped to conveniently distinguish Crystalline Form II of Verubecestat from other crystalline forms. Selections of such characteristic peaks are set out in Table 2, (wherein each peak location is +/−0.2° 2 theta).

TABLE 2

| Peak Location Group No. | Peak Location (degrees 2 theta (+/−0.2° 2 theta)) | d-spacing (angstroms) |
|---|---|---|
| Group 1 | 10.94 | 8.09 |
|  | 14.98 | 5.92 |
| Group 2 | 10.94 | 8.09 |
|  | 14.98 | 5.92 |
|  | 14.53 | 6.10 |
|  | 16.23 | 5.46 |
|  | 16.63 | 5.33 |
|  | 26.18 | 3.40 |
| Group 3 | 10.94 | 8.09 |
|  | 14.53 | 6.10 |
|  | 14.98 | 5.92 |
|  | 16.23 | 5.46 |
|  | 16.63 | 5.33 |
|  | 17.77 | 4.99 |
|  | 21.77 | 4.08 |
|  | 23.24 | 3.83 |
|  | 26.18 | 3.40 |
| Group 4 | 10.94 | 8.09 |
|  | 14.53 | 6.10 |
|  | 14.98 | 5.92 |
|  | 16.23 | 5.46 |
|  | 16.63 | 5.33 |
|  | 17.77 | 4.99 |
|  | 20.84 | 4.26 |
|  | 21.77 | 4.08 |
|  | 23.24 | 3.83 |
|  | 26.18 | 3.40 |
|  | 30.88 | 2.90 |
|  | 33.39 | 2.68 |

Thus, in another aspect, Crystalline Form II of Verubecestat is characterized by Peak Location Group 1 of Table 2, wherein the PXRD pattern obtained as described above exhibits at least the two listed characteristic PXRD peak locations of Group 1, (each +/−0.2° 2-theta). In another aspect, Crystalline Form II of Verubecestat is characterized by Peak Location Group 2 of Table 2, wherein the PXRD pattern obtained as described above exhibits at least the two characteristic PXRD peak locations of Group No. 1 and from one to four (in another aspect from two to four, and in yet another aspect from three to four) of the additional peak locations listed in Group 2, (each +/−0.2° 2-theta). In another aspect, Crystalline Form II of Verubecestat is characterized by Peak Location Group 2 of Table 2, wherein the PXRD pattern obtained as described above exhibits at least the two characteristic PXRD peak locations of Group No. 1 and each of the four additional peak locations listed in Group 2, (each +/−0.2° 2-theta).

In another aspect, Crystalline Form II of Verubecestat is characterized by Peak Location Group 3 of Table 2, wherein the PXRD pattern obtained as described above exhibits at least the exhibits at least the PXRD peak locations of Group No. 2 and from one to three (in yet another aspect from two to three) of the additional peak locations listed in Group 3, (each +/−0.2° 2-theta). In another aspect, Crystalline Form II of Verubecestat is characterized by Peak Location Group 3 of Table 2, wherein the PXRD pattern obtained as described above exhibits at least the six characteristic PXRD peak locations of Group No. 2 and each of the three additional peak locations listed, (each +/−0.2° 2-theta).

In another aspect, Crystalline Form II of Verubecestat is characterized by Peak Location Group 4 of Table 2, wherein the PXRD pattern obtained as described above exhibits at least the nine characteristic PXRD peak locations of Group No. 3 and from one to three (in yet another aspect from two to three) of the additional peak locations listed, (each +/−0.2° 2-theta). In another aspect, Crystalline Form II of Verubecestat is characterized by Peak Location Group 4 of Table 2, wherein the PXRD pattern obtained as described above exhibits at least the nine characteristic PXRD peak locations of Group No. 3 and each of the three additional peak locations listed, (each +/−0.2° 2-theta).

Differential Scanning Calorimetry

A differential scanning calorimeter (DSC) was used to monitor thermal events as a function of temperature increase. The DSC data reported herein were acquired using a using TA Instruments DSC 2910 or equivalent. A suitable amount of sample was weighed into a pan, covered and placed at the sample position in the calorimeter cell. An empty pan was placed at the reference position. The calorimeter cell was closed and a flow of nitrogen was passed through the cell. The heating program was set to heat the sample at a heating rate of 10° C./min to a temperature that is above all thermal events. When the run was completed, the data were analyzed using the DSC analysis program contained in the system software. The thermal events were integrated between baseline temperature points that were above and below the temperature range over which the thermal event was observed. The data reported were the onset temperature, peak temperature and enthalpy. Those skilled in the art will appreciate that the accuracy of measurements will vary within a margin of error. The accuracy of the measured sample temperature with this method is within +/−1° C. The heat flow, which was normalized by a sample weight, was plotted versus the measured sample temperature. The data were reported in units of watts/gram ("W/g"). The plot was made with the endothermic peaks pointing down.

Figure 2:
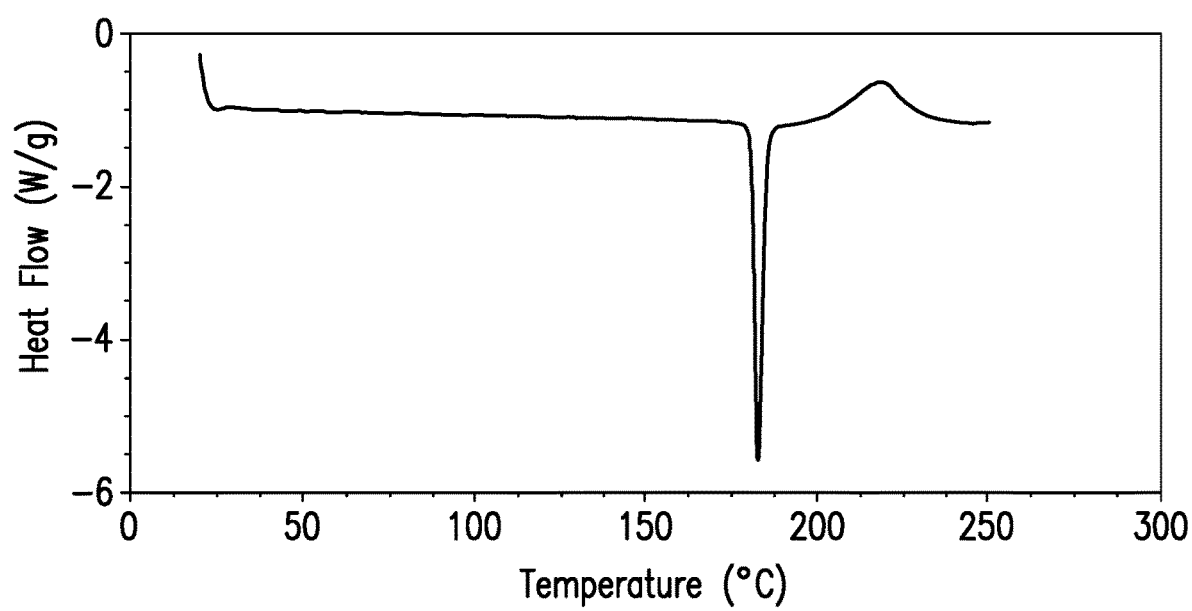
FIG. 2 is a graph of a differential scanning calorimetry ("DSC") thermogram of Crystalline Form II of Verubecestat. The graph plots the normalized heat flow in units of Watts/gram (W/g) versus the measured sample temperature (° C.) with exotherms up.

Using the differential scanning calorimetry (DSC) equipment and procedures described above, the Crystalline Form II of Verubecestat was subjected to DSC analysis. FIG. 2 depicts a typical DSC curve of Crystalline Form II of Verubecestat. FIG. 2 shows a single sharp melting endotherm with an extrapolated onset temperature of 181.7° C. and a peak temperature of 183.5° C., which is indicative of a single crystalline species. (The sample appears to decompose above approximately 200° C., as indicated by the DSC thermogram.)

These melt temperatures can be used, alone or in combination with any of the other characterizations described herein, to identify Crystalline Form II of Verubecestat and to distinguish it from other crystal forms of verubecestat. Thus, in another aspect, Crystalline Form II of Verubecestat is characterized by a melting endotherm with a peak temperature at 183.5° C. (+/−1° C.) as measured by DSC. In another aspect, Crystalline Form II of Verubecestat is characterized by a melting endotherm with an extrapolated onset temperature of 181.7° C. (+/−1° C.) and a melting endotherm with a peak temperature at 183.5° C. (+/−1° C.) as measured by DSC. In another aspect, Crystalline Form II of Verubecestat is characterized by the DSC curve substantially as shown in FIG. 2.

In yet another aspect, Crystalline Form II of Verubecestat is characterized by any of the these DSC measurements and/or the DSC curve substantially as shown in FIG. 2, alone or in combination with any of the other characterizations described herein. Thus, in yet another aspect, Crystalline Form II of Verubecestat is characterized by PXRD Peak Location Group 1, or by PXRD Peak Location Group 2, or by PXRD Peak Location Group 3, or by PXRD Peak Location Group 4, each as described above, and each further characterized as exhibiting a peak temperature at 183.5° C. (+/−1° C.), measured by differential scanning calorimetry.

In yet another aspect, Crystalline Form II of Verubecestat is characterized by PXRD Peak Location Group 1, or by PXRD Peak Location Group 2, or by PXRD Peak Location Group 3, or by PXRD Peak Location Group 4, each as described above, and each further characterized as exhibiting a melting endotherm with an extrapolated onset temperature of 181.7° C. (+/−1° C.) and a peak temperature at 183.5° C. (+/−1° C.), measured by differential scanning calorimetry.

In yet another aspect, Crystalline Form II of Verubecestat is characterized by PXRD Peak Location Group 1, or by PXRD Peak Location Group 2, or by PXRD Peak Location Group 3, or by PXRD Peak Location Group 4, each as described above, and each further characterized by the DSC curve substantially as shown in FIG. 2.

Solid State NMR

Solid State $^{13}$C nuclear magnetic resonance (NMR) data reported herein were acquired on a Bruker AV400 NMR spectrometer operating at a $^1$H resonance frequency of 500.14 MHz, using a Bruker 4 mm H/F/X BB triple resonance CPMAS probe and an MAS rate of 13 kHz. The experiment temperature was controlled with a Bruker VT control unit and set to 270 degrees Kelvin (degrees K). Based on temperature calibration experiments, a set temperature of 270 K corresponds to an actual sample temperature of 295 K. All $^{13}$C spectra were externally referenced using a sample of glycine with the carboxylic carbon in glycine assumed at 176.70 ppm. A Lorentzian line broadening of 30 Hz and zero filling to 32 k data points were applied to all $^{13}$C spectra before Fourier Transformation.

The $^{13}$C Cross Polarization Magic Angle Spinning (CP-MAS) spectra were collected utilizing 100 kHz 1H π/2 excitation pulses. The $^1$H pulse power was ramped up linearly from 47 kHz to 83 kHz over a 3 ms contact time, to enhance CP efficiency. The pulse power of the $^{13}$C square CP pulse was matched to the $^1$H ramp to produce maximum signal. High-power TPPM $^1$H decoupling at 100 kHz was applied during $^{13}$C data acquisition. The pulse delay time used and number of scans acquired for signal averaging were 9.0 s and 4096, respectively.

Figure 4:
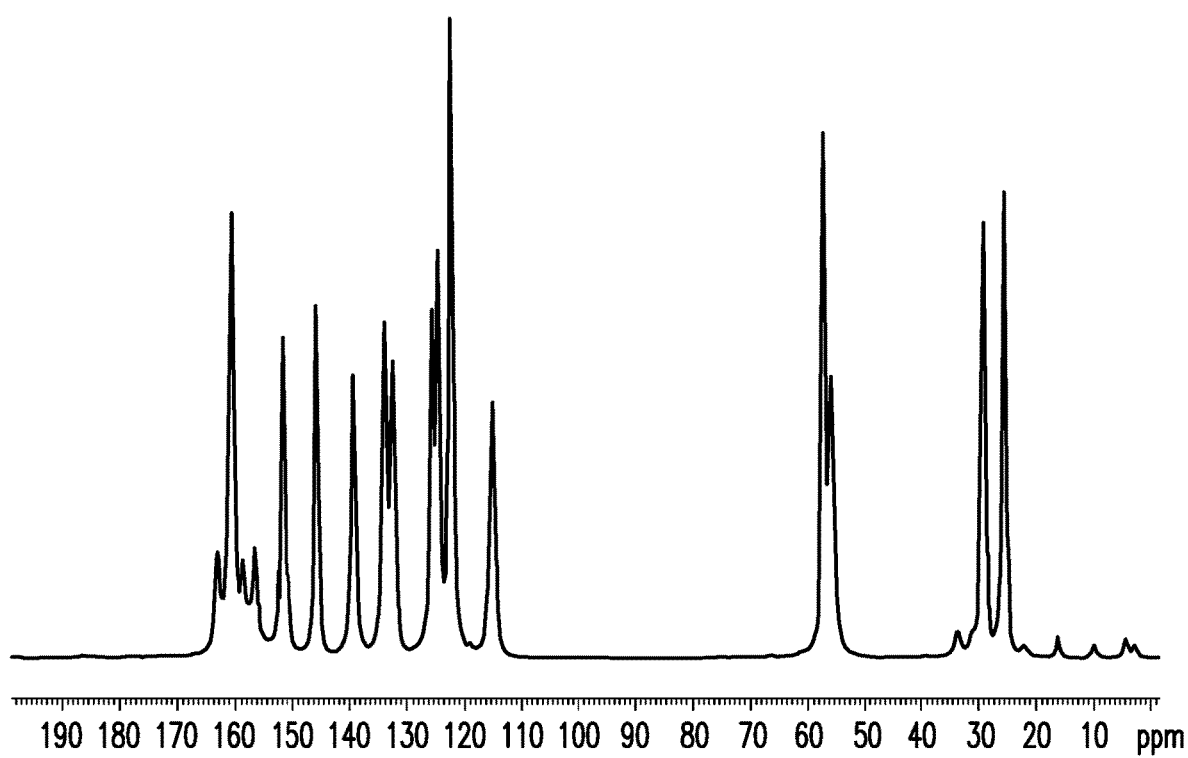
FIG. 4 depicts a solid state NMR (nuclear magnetic resonance) spectrum of Crystalline Form II of verubecestat.

Using the $^{13}$C solid state NMR equipment and procedures described above, the solid state $^{13}$C (carbon-13) CPMAS NMR spectrum for the Crystalline Form II of verubecestat was obtained. These data are shown in FIG. 4. Characteristic peaks for Crystalline Form II of Verubecestat are observed at 162.98, 160.46, 158.65, 156.39, 151.47, 145.63, 139.21, 133.72, 132.28, 125.50, 124.38, 122.10, 114.93, 57.11, 55.82, 29.22 and 25.66 ppm. This NMR measurement can be used, alone or in combination with any of the other characterizations described herein, to identify Crystalline Form II of Verubecestat and to distinguish it from other crystal forms of verubecestat. Thus, in another aspect, Crystalline Form II of Verubecestat is characterized by a solid state $^{13}$C (carbon-13) CPMAS NMR spectrum as shown in FIG. 4. In another aspect, Crystalline Form II of Verubecestat is characterized by a solid state $^{13}$C (carbon-13) CPMAS NMR spectrum having peaks at 162.98, 160.46, 158.65, 156.39, 151.47, 145.63, 139.21, 133.72, 132.28, 125.50, 124.38, 122.10, 114.93, 57.11, 55.82, 29.22 and 25.66 ppm.

In yet another aspect, Crystalline Form II of Verubecestat is characterized by the above described NMR characteristic peaks and/or the data shown in FIG. 4, alone or in combination with any of the other characterizations described herein.

Thus, in yet another aspect, Crystalline Form II of Verubecestat is characterized by PXRD Peak Location Group 1, or by PXRD Peak Location Group 2, or by PXRD Peak Location Group 3, or by PXRD Peak Location Group 4, each as described above, and each further characterized by a solid state $^{13}$C (carbon-13) CPMAS NMR spectrum having peaks at 162.98, 160.46, 158.65, 156.39, 151.47, 145.63, 139.21, 133.72, 132.28, 125.50, 124.38, 122.10, 114.93, 57.11, 55.82, 29.22 and 25.66 ppm.

In yet another aspect, Crystalline Form II of Verubecestat is characterized by PXRD Peak Location Group 1, or by PXRD Peak Location Group 2, or by PXRD Peak Location Group 3, or by PXRD Peak Location Group 4, each as described above, and each further characterized by a solid state $^{13}$C (carbon-13) CPMAS NMR spectrum substantially as shown in FIG. 4.

In another aspect, Crystalline Form II of Verubecestat is characterized by PXRD Peak Location Group 1, or by PXRD Peak Location Group 2, or by PXRD Peak Location Group 3, or by PXRD Peak Location Group 4, each as described above, and each further characterized by a solid state $^{13}$C (carbon-13) CPMAS NMR spectrum having peaks at 162.98, 160.46, 158.65, 156.39, 151.47, 145.63, 139.21, 133.72, 132.28, 125.50, 124.38, 122.10, 114.93, 57.11, 55.82, 29.22 and 25.66 ppm, or by a solid state $^{13}$C (carbon-13) CPMAS NMR spectrum substantially as shown in FIG. 4, and each further characterized by a melting endotherm with a peak temperature at 183.5° C. (+/−1° C.) as measured by DSC.

In another aspect, Crystalline Form II of Verubecestat is characterized by PXRD Peak Location Group 1, or by PXRD Peak Location Group 2, or by PXRD Peak Location Group 3, or by PXRD Peak Location Group 4, each as described above, and each further characterized by a solid state $^{13}$C (carbon-13) CPMAS NMR spectrum having peaks at 162.98, 160.46, 158.65, 156.39, 151.47, 145.63, 139.21, 133.72, 132.28, 125.50, 124.38, 122.10, 114.93, 57.11, 55.82, 29.22 and 25.66 ppm, or by a solid state $^{13}$C (carbon-13) CPMAS NMR spectrum substantially as shown in FIG. 4, and each further characterized by a melting endotherm with an extrapolated onset temperature of 181.7° C. (+/−1° C.) and a melting endotherm with a peak temperature at 183.5° C. (+/−1° C.) as measured by DSC.

In another aspect, Crystalline Form II of Verubecestat is characterized by PXRD Peak Location Group 1, or by PXRD Peak Location Group 2, or by PXRD Peak Location Group 3, or by PXRD Peak Location Group 4, each as described above, and each further characterized by a solid state $^{13}$C (carbon-13) CPMAS NMR spectrum having peaks at 162.98, 160.46, 158.65, 156.39, 151.47, 145.63, 139.21, 133.72, 132.28, 125.50, 124.38, 122.10, 114.93, 57.11, 55.82, 29.22 and 25.66 ppm, or by a solid state $^{13}$C (carbon-13) CPMAS NMR spectrum substantially as shown in FIG. 4, and each further characterized by a melting endotherm with substantially as shown in FIG. 2.

Single-Crystal X-Ray Structure

Figure 5:
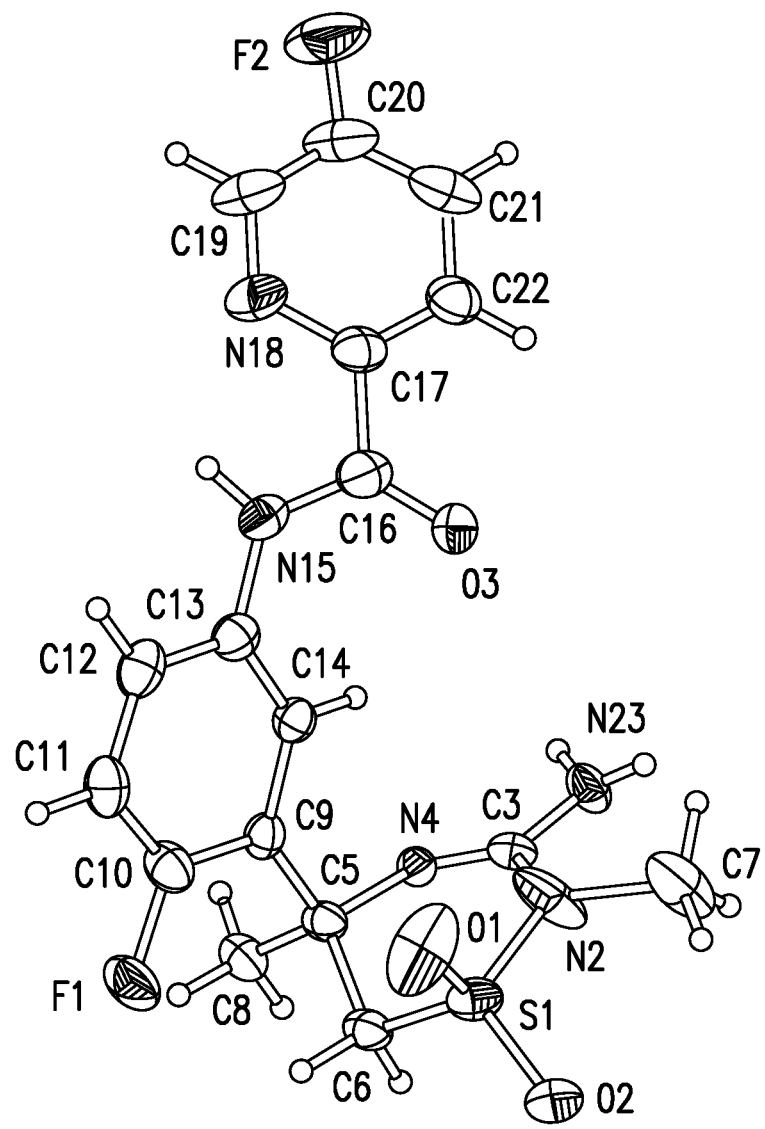
FIG. 5 is an ORTEP representation of the single crystal structure of Crystalline Form II of Verubecestat generated from the crystallographic coordinates shown in Table 4.

The single crystal structure of Crystalline Form II of Verubecestat was determined. The acquisition and cell parameters that were determined for Crystalline Form II of Verubecestat are shown in Table 3. FIG. 5 is an ORTEP representation of the molecule generated from the crystallographic coordinates. ORTEP is an abbreviation of Oak Ridge Thermal Ellipsoid Plot, a representation of molecular structure as determined by x-ray diffraction. The ORTEP drawing provides the exact position in space of every atom within the crystal and can be used to generate a complete three dimensional image of the crystal. As can be seen, the ORTEP drawing indicates that Crystalline Form II of Verubecestat appears to exist substantially in the amino tautomeric form. This crystal structure can be used, alone or in combination with any of the other characterizations described herein, to identify Crystalline Form II of Verubecestat and to distinguish it from other crystal forms of verubecestat. Thus, in another aspect, Crystalline Form II of Verubecestat is characterized by the ORTEP depicted in FIG. 5. In another aspect, Crystalline Form II of Verubecestat is characterized by the single crystal structure values shown in Table 3.

Figure 3:
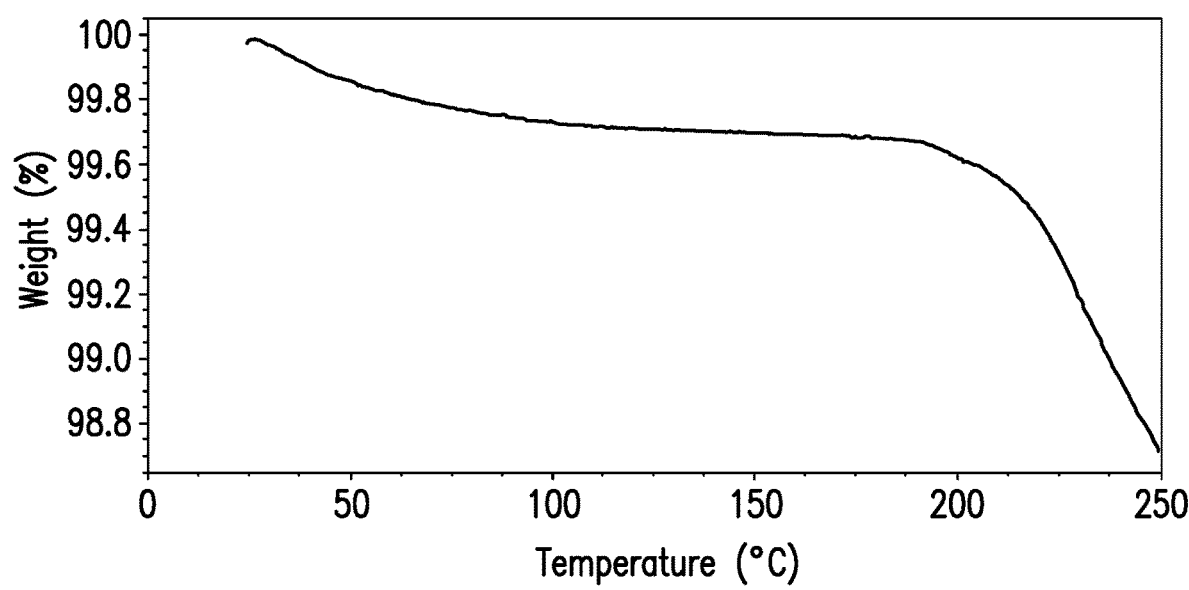
FIG. 3 is a graph of a thermal gravimetric analysis ("TGA") of Crystalline Form II of verubecestat. The graph plots the weight (percentage) against temperature (° C.).

In yet another aspect, Crystalline Form II of Verubecestat is alternatively characterized by the ORTEP depicted in FIG. 5 or the single crystal structure information shown in Table 3, alone and/or in combination with each of the aspects of PXRD characterizations described above, and/or each of the DSC aspects described above, and/or with the NMR characteristic peaks described above and/or with the NMR data shown in FIG. 4, and/or with any of the TGA measurements and/or with the TGA curve substantially as shown in FIG. 3.

TABLE 3

| Crystal system | Tetragonal | |
|---|---|---|
| Space group | P4₁2₁2 | |
| Unit cell dimensions | a = 12.2581(4) Å | α = 90°. |
| | b = 12.2581(4) Å | β = 90°. |
| | c = 24.6362(9) Å | γ = 90°. |
| Volume | 3701.9(3) Å³ | |
| Z | 8 | |
| Density (calculated) | 1.469 Mg/m³ | |

In yet another aspect, Crystalline Form II of Verubecestat is characterized by the above described single crystal structure (described in Table 3 and/or as depicted by the ORTEP of FIG. 5) alone or in combination with any of the other characterizations described herein.

Thus, in yet another aspect, Crystalline Form II of Verubecestat is characterized by PXRD Peak Location Group 1, or by PXRD Peak Location Group 2, or by PXRD Peak Location Group 3, or by PXRD Peak Location Group 4, each as described above, and each further characterized by the single crystal structure described in Table 3 or in FIG. 5.

In yet another aspect, Crystalline Form II of Verubecestat is characterized by PXRD Peak Location Group 1, or by PXRD Peak Location Group 2, or by PXRD Peak Location Group 3, or by PXRD Peak Location Group 4, each as described above, and each further characterized by the single crystal structure described in Table 3 or in FIG. 5., and each further characterized by a solid state $^{13}C$ (carbon-13) CPMAS NMR spectrum having peaks at 162.98, 160.46, 158.65, 156.39, 151.47, 145.63, 139.21, 133.72, 132.28, 125.50, 124.38, 122.10, 114.93, 57.11, 55.82, 29.22 and 25.66 ppm.

In yet another aspect, Crystalline Form II of Verubecestat is characterized by PXRD Peak Location Group 1, or by PXRD Peak Location Group 2, or by PXRD Peak Location Group 3, or by PXRD Peak Location Group 4, each as described above, and each further characterized by the single crystal structure described in Table 3 or in FIG. 5., and each further characterized by a solid state $^{13}C$ (carbon-13) CPMAS NMR spectrum substantially as shown in FIG. 3.

In yet another aspect, Crystalline Form II of Verubecestat is characterized by PXRD Peak Location Group 1, or by PXRD Peak Location Group 2, or by PXRD Peak Location Group 3, or by PXRD Peak Location Group 4, each as described above, and each further characterized by the single crystal structure described in Table 3 or in FIG. 5., and each further characterized by a solid state $^{13}C$ (carbon-13) CPMAS NMR spectrum having peaks at 162.98, 160.46, 158.65, 156.39, 151.47, 145.63, 139.21, 133.72, 132.28, 125.50, 124.38, 122.10, 114.93, 57.11, 55.82, 29.22 and 25.66 ppm, or by a solid state $^{13}C$ (carbon-13) CPMAS NMR spectrum substantially as shown in FIG. 4, and each further characterized by a melting endotherm with a peak temperature at 183.5° C. (+/−1° C.) as measured by DSC.

In yet another aspect, Crystalline Form II of Verubecestat is characterized by PXRD Peak Location Group 1, or by PXRD Peak Location Group 2, or by PXRD Peak Location Group 3, or by PXRD Peak Location Group 4, each as described above, and each further characterized by the single crystal structure described in Table 3 or in FIG. 5., and each further characterized by a solid state $^{13}C$ (carbon-13) CPMAS NMR spectrum having peaks at 162.98, 160.46, 158.65, 156.39, 151.47, 145.63, 139.21, 133.72, 132.28, 125.50, 124.38, 122.10, 114.93, 57.11, 55.82, 29.22 and 25.66 ppm, or by a solid state $^{13}C$ (carbon-13) CPMAS NMR spectrum substantially as shown in FIG. 4, and each further characterized by a melting endotherm with an extrapolated onset temperature of 181.7° C. (+/−1° C.) and a melting endotherm with a peak temperature at 183.5° C. (+/−1° C.) as measured by DSC.

In yet another aspect, Crystalline Form II of Verubecestat is characterized by PXRD Peak Location Group 1, or by PXRD Peak Location Group 2, or by PXRD Peak Location Group 3, or by PXRD Peak Location Group 4, each as described above, and each further characterized by the single crystal structure described in Table 3 or in FIG. 5., and each further characterized by a solid state $^{13}C$ (carbon-13) CPMAS NMR spectrum having peaks at 162.98, 160.46, 158.65, 156.39, 151.47, 145.63, 139.21, 133.72, 132.28, 125.50, 124.38, 122.10, 114.93, 57.11, 55.82, 29.22 and 25.66 ppm, or by a solid state $^{13}C$ (carbon-13) CPMAS NMR spectrum substantially as shown in FIG. 4, and each further characterized by a melting endotherm with substantially as shown in FIG. 2.

Thermogravimetric Analysis

Thermal gravimetric analysis (TGA) data were acquired using a Perkin Elmer model TGA 7 or equivalent. Experiments were performed under a flow of nitrogen and using a heating rate of 10° C./min to a maximum temperature of approximately 250° C. After automatically taring the balance, an appropriate amount of sample was added to the platinum pan, the furnace raised, and the heating program started. Analysis of the results were carried out by selecting the Delta Y function within the instrument software and choosing the temperatures between which the weight loss is to be calculated. Weight losses were reported up to the onset of decomposition/evaporation.

Using the thermogravimetric analysis (TGA) equipment and procedures described above, Crystalline Form II of Verubecestat was subjected to TGA analysis. FIG. 3 shows a typical TGA analysis curve for Crystalline Form II of verubecestat. The data show 0.5 wt. % loss up to 150° C., followed by thermal decomposition above 200° C. This TGA analysis can be used, alone or in combination with any of the other characterizations described herein, to identify Crystalline Form II of Verubecestat and to distinguish it from other crystal forms of verubecestat. Thus, in another aspect, Crystalline Form II of Verubecestat is characterized by a TGA curve substantially as shown in FIG. 3. In yet another aspect, Crystalline Form II of Verubecestat is characterized by any of these TGA measurements and/or the TGA curve substantially as shown in FIG. 3, alone or in combination with any of the other characterizations described herein, including each of the aspects of PXRD characterizations described above, and/or each of the DSC aspects described above.

Properties

The Crystalline Form II of Verubecestat described and characterized herein exhibits excellent physical properties while minimizing the difficulties associated with drug product manufacturing, processing and storage. For example, Crystalline Form II of Verubecestat exhibits unexpectedly improved thermodynamic stability and comparable chemical stability in drug product (tablet formulation) compared to crystalline Form I of verubecestat while remaining a BCS Class I category substance. Despite its desirable properties, Crystalline Form II of Verubecestat did not appear during routine polymorph screening; it was surprisingly and advantageously invented after many batches of other crystalline forms (such as Crystalline Anhydrous Form I described in WO2016/025364) were produced using multiple synthetic routes in a variety of conditions at multiple manufacturing sites.

The thermodynamic stability of Crystalline Form II of Verubecestat was assessed using competitive slurry experiments in various solvent systems. Crystalline Form I of Verubecestat, obtained using the procedures set out in WO2016025364, and Crystalline Form II of verubecestat material obtained as described above were slurried in various solvents for an extended period of time and at a controlled temperature. At the end of the experiments, the solvent was removed and the remaining crystalline material were evaluated using Powder X-ray Diffraction (PXRD) to confirm the resultant form. Typically the more stable form will remain and the less stable form will convert to the more stable form. In all cases, Crystalline Form II of Verubecestat was the only form remaining and thus the more stable form.

To assess the chemical stability of Crystalline Form II of verubecestat in the tablet formulation, a 4 week open dish accelerated stability experiment was performed at a controlled temperature and humidity. Identical measurements were made to Crystalline Form I of verubecestat, which Form I is described in WO2016025364 for comparison. (12 mg tablets were used because the available stability data for tablets comprising Form I of verubecestat indicated that 12 mg tablet is more susceptible to degradation than the 40 mg tablet.) Thus, 12 mg tablets of Crystalline Form I of verubecestat and 12 mg tablets of Crystalline Form II of Verubecestat were placed in an open dish and the temperature maintained at 40° C. and 75% relative humidity (RH) for four weeks. At the end of two weeks and of four weeks, tablets were analyzed using HPLC. The data obtained are reported in the following table, where "Hyd1" and "Hyd2" indicate observed degradation product:

TABLE 1

Chemical Stability of 12 mg Tablets Stored in Open Dish at 40° C./75% RH

| Time Point | Crystalline Form I | | | | Crystalline Form II | | | |
| --- | --- | --- | --- | --- | --- | --- | --- | --- |
| | Assay (% LC) | Degradation Product (%) | | | Assay (% LC) | Degradation Product (%) | | |
| | | Hyd1 | Hyd2 | Total | | Hyd1 | Hyd2 | Total |
| 0 | 98.5 | — | — | — | 104.3 | — | — | — |
| 2 weeks | 98.5 | 0.30 | 0.16 | 0.46 | 104.6 | 0.21 | 0.10 | 0.31 |
| 4 weeks | 97.4 | 0.52 | 0.26 | 0.78 | 102.4 | 0.39 | 0.18 | 0.56 |

"—" means not more than 0.05%

As can be seen from the data reported in the table above, Crystalline Form II of Verubecestat unexpectedly exhibited comparable amounts of degradation product at each time-point compared with Crystalline Form I of verubecestat while exhibiting improved thermodynamic stability. Additionally, the melting point of Crystalline Form II was measured at above 180 C. By comparison, the melting point of Crystalline Form I was measured at 160 C. The higher melting point of Crystalline Form II is further indication of superior thermal stability.

Crystalline Form II of Verubecestat exhibits good chemical stability and is more thermodynamically stable compared to Form I of verubecestat while maintaining a preferred BCS (Biopharmaceutics Classification System) designation as a Class 1 substance. Accordingly, compositions comprising the Crystalline Form II of Verubecestat may be synthesized using a crystallization process that is more efficient and results in improved particle size and morphology relative to other known forms of verubecestat. Employing a novel crystalline form of verubecestat according to the invention may allow the use of conventional processing methods and formulation strategies. This is significant in that Crystalline Form II of Verubecestat exhibits a reduced physical stability risk compared to higher energy state forms. Ultimately this may allow for less protective and potentially less expensive packaging configurations. A conventional formulation also allows for the use of standard, well-known processing trains (fluidized bed granulation, blending, and compression). These standard processing trains have been optimized to provide high yield, are easily scalable, and are abundant throughout the pharmaceutical manufacturing facilities worldwide. In addition, the manufacture of non-standard formulations of verubecestat may require higher energy inputs (extrusion) or the use of solvents (e.g., spray drying). Thus, the novel Crystalline Form II of Verubecestat may provide a potential for improved overall cost of goods.

Pharmaceutical Compositions

As noted above, another embodiment provides a pharmaceutical composition comprising Crystalline Form II of Verubecestat (as characterized by any of the characterizations, alone or in combination, described herein). In such compositions, Crystalline Form II comprises either the sole active agent, or is optionally present in combination with one or more additional therapeutic agents. In either case, said pharmaceutical compositions can further comprise one or more pharmaceutically acceptable carriers, excepients and/or diluents. Non-limiting examples of additional therapeutic agents which may be useful in combination with a Crystalline Form II of Verubecestat are described in WO2011/044181 and include those selected from the group consisting of: (a) drugs that may be useful for the treatment of Alzheimer's disease and/or drugs that may be useful for treating one or more symptoms of Alzheimer's disease, (b) drugs that may be useful for inhibiting the synthesis Aβ, (c) drugs that may be useful for treating neurodegenerative diseases, and (d) drugs that may be useful for the treatment of type II diabetes and/or one or more symptoms or associated pathologies thereof.

Additional non-limiting examples of therapeutic agents which may be useful in combination with a Crystalline Form II of Verubecestat include drugs that may be useful for the treatment, prevention, delay of onset, amelioration of any pathology associated with Aβ and/or a symptom thereof. Non-limiting examples of pathologies associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $β_2$ microglobulins and complications arising therefrom in hemodialysis patients), scrapie, bovine spongiform encephalitis, and Creutzfeld-Jakob disease, comprising administering to said patient Crystalline Form II of Verubecestat in an amount effective to inhibit or treat said pathology or pathologies.

Additional non-limiting examples of therapeutic agents that may be useful in combination with Crystalline Form II of Verubecestat include: muscarinic antagonists (e.g., $m_1$ agonists (such as acetylcholine, oxotremorine, carbachol, or McNa343), or $m_2$ antagonists (such as atropine, dicycloverine, tolterodine, oxybutynin, ipratropium, methoctramine, tripitamine, or gallamine)); cholinesterase inhibitors (e.g., acetyl- and/or butyrylchlolinesterase inhibitors such as donepezil (Aricept®), (±)-2,3-dihydro-5,6-dimethoxy-2-[[1-(phenylmethyl)-4-piperidinyl]methyl]-1H-inden-1-one hydrochloride), galantamine (Razadyne®), and rivastigimine (Exelon®); N-methyl-D-aspartate receptor antagonists (e.g., Namenda® (memantine HCl, available from Forrest Pharmaceuticals, Inc.); combinations of cholinesterase inhibitors and N-methyl-D-aspartate receptor antagonists; gamma secretase modulators; gamma secretase inhibitors; non-steroidal anti-inflammatory agents; anti-inflammatory agents that can reduce neuroinflammation; anti-amyloid antibodies (such as bapineuzemab, Wyeth/Elan); vitamin E; nicotinic acetylcholine receptor agonists; CB1 receptor inverse agonists or CB1 receptor antagonists; antibiotics; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Tau kinase inhibitors (e.g., GSK3beta inhibitors, cdk5 inhibitors, or ERK inhibitors); Tau aggregation inhibitors (e.g., Rember®); RAGE inhibitors (e.g., TTP 488 (PF-4494700)); anti-Abeta vaccine; APP ligands; agents that upregulate insulin, cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., Simcor® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux such as gelsolin; Metal-protein attenuating compound (e.g., PBT2); and GPR3 modulators; and antihistamines such as Dimebolin (e.g., Dimebon®, Pfizer).

When used in combination with additional therapeutic agents, Crystalline Form II of Verubecestat and the one or more additional agents may be administered together or sequentially, as noted above. When used contemporaneously with one or more other drugs, a pharmaceutical composition in unit dosage form containing such other drugs and the Crystalline Form II is contemplated. However, the combination therapy may also include therapies in which the Crystalline Form II of Verubecestat and one or more other drugs are administered on different overlapping schedules. It is also contemplated that when used in combination with one or more other active ingredients, Crystalline Form II of Verubecestat and the other active ingredient(s) may be used in lower doses than when each is used singly. Further, such other drugs may be administered by a route and in an amount commonly used therefor, contemporaneously or sequentially with Crystalline Form II of verubecestat. When Crystalline Form II is used contemporaneously with one or more other drugs, a pharmaceutical composition comprising such other drugs in addition to the Crystalline Form II are prepared without undue experimentation in accordance with the methods described herein and/or known in the art.

The weight ratio of Crystalline Form II to the second active ingredient may be varied and will depend upon the effective dose of each ingredient. Generally, an effective dose of each is used. Thus, for example, when Crystalline Form II of Verubecestat is combined with another agent, the weight ratio of the Crystalline Form II and the second agent will generally range from about 1000:1 to about 1:1000, such as about 200:1 to about 1:200, wherein, in each case an effective dose for the intended purpose is used. Such combinations may be administered separately or concurrently, and the administration of one may be prior to, concurrent with, or subsequent to the administration of the other agent(s).

For preparing the pharmaceutical compositions described herein, pharmaceutically acceptable carriers can be solid or liquid, or in any other known dosage form such as aerosols or lotions. Non-limiting examples of solid form preparations include powders, tablets, dispersible granules, capsules, cachets and suppositories. The powders and tablets may be comprised of any of the weight % values of active ingredient described herein, and in any desired dose (e.g., doses as described herein).

Crystalline Form II of Verubecestat may conveniently be presented in a dosage unit form which may be prepared by any of the methods well known in art of pharmacy. All methods include the step of bringing Crystalline Form II into association with the carrier which constitutes accessory ingredients. In general, the pharmaceutical compositions are prepared by uniformly and intimately bringing active ingredient into association with a liquid carrier or finely divided solid carrier or both, and then, if necessary, shaping the product into the desired formulation. In the pharmaceutical composition active ingredient(s) is included in an effective amount. "Effective amount" or "therapeutically effective amount" is meant to describe an amount of Crystalline Form II of Verubecestat effective to elicit the biological or medical response of a tissue, system, animal or human, that is being sought by the researcher, medical doctor, veterinarian, or other clinician. It is recognized that one skilled in the art may affect the disorders by treating a patient presently afflicted with the disorders or by prophylactically treating a patient at risk for the disease or disorder with an effective amount of Crystalline Form II of verubecestat. As used herein, the terms "treatment" or "treating" refer to all processes wherein there may be a slowing, interrupting, arresting, controlling, or stopping of the progression of the diseases or disorders described herein, but does not necessarily indicate a total elimination of all disorder pathologies or symptoms, as well as the prophylactic therapy of the mentioned conditions, particularly in a patient who is predisposed to such disease or disorder. In the case of Alzheimer's disease, treatments can be directed to persons who have been diagnosed with Alzheimer's disease, or those with MCI (Mild Cognitive Impairment) or prodromal Alzheimer's disease, or prior to such diagnosis in those who are (or are suspected of being) at risk of developing Alzheimer's disease who, as directed by the attending healthcare professional. The terms "administration of" and/or "administering a Crystalline Form II of verubecestat should be understood to mean providing a Crystalline Form II, or a composition comprising Crystalline Form II, to an individual in need thereof.

Pharmaceutical compositions intended for oral use may be prepared in accordance with methods described herein and other methods well known to art for the manufacture of pharmaceutical compositions. Such compositions may further contain active agents selected from sweetening agents, flavoring agents, coloring agents and preserving agents where pharmaceutically elegant and/or palatable preparations are desired. Tablets and capsules are contemplated. Tablets or capsules may contain active ingredient in admixture with non-toxic pharmaceutically acceptable excipients which are suitable for the manufacture of tablets. These excipients may be for example, inert diluents, such as calcium carbonate, sodium carbonate, mannitol, micrystalline cellulose, starch, lactose (e.g., lactose monohydrate or lactose anhydrate), calcium phosphate or sodium phosphate; granulating or disintegrating agents, for example, crospovidone, corn starch, croscarmellose sodium or alginic acid; binding agents, for example starch, hydroxypropylcellulose (HPC), hydroxypropylmethyl cellulose (HPMC), silicone dioxide, gelatin or acacia, and lubricating agents, for example magnesium stearate, stearic acid or talc. Suitable solid carriers also may include magnesium carbonate, magnesium stearate, talc, sugar or lactose. Tablets, powders, cachets and capsules can be used as solid dosage forms suitable for oral administration. The tablets may be uncoated or coated by known techniques to delay disintegration and absorption in the gastrointestinal tract and thereby provide sustained action over a longer period. Compositions for oral use may also be presented as hard gelatin capsules wherein active ingredient is mixed with an inert solid diluent, for example, calcium carbonate, calcium phosphate or kaolin, or as soft gelatin capsules wherein active ingredient is mixed with water or an oil medium, for example peanut oil, liquid paraffin, or olive oil. Aqueous suspensions contain active materials in admixture with excipients suitable for the manufacture of aqueous suspensions. Dispersible powders and granules suitable for preparation of an aqueous suspension by addition of water provide active ingredient in admixture with a dispersing or wetting agent, suspending agent, and one or more preservatives.

Liquid and topical form preparations are also contemplated. Such forms include solutions, suspensions and emulsions. Non-limiting examples which may be useful include water or water-propylene glycol solutions for parenteral injection or addition of sweeteners and opacifiers for oral solutions, suspensions and emulsions. Liquid form preparations may also include solutions for intranasal administration. Aerosol preparations suitable for inhalation are also contemplated. Such forms include solutions and solids in powder form, which may be in combination with a pharmaceutically acceptable carrier, such as an inert compressed gas, e.g. nitrogen. Solid form preparations that are intended to be converted, shortly before use, to liquid form preparations for either oral or parenteral administration are also contemplated. Such liquid forms include solutions, suspensions and emulsions. Transdermal delivery preparations are also contemplated. Transdermal compositions can take the form of creams, lotions, aerosols and/or emulsions and can be included in a transdermal patch of the matrix or reservoir type as are conventional in art for this purpose. Subcutaneous delivery forms are also contemplated. Additional examples of dosage forms, formulations, and pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Another embodiment provides suitable dosages and dosage forms of Crystalline Form II of Verubecestat and its use in the various methods described herein. Suitable doses for administering Crystalline Form II of Verubecestat to patients may readily be determined by those skilled in art, e.g., by an attending physician, pharmacist, or other skilled worker, and may vary according to patient health, age, weight, frequency and duration of administration, use with other active ingredients, and/or indication for which the Crystalline Form II is administered. Thus, the dosage of active ingredient in the compositions of this invention may be varied, however, it is necessary that the amount of the active ingredient be such that a suitable dosage form is obtained. The doses may be administered to patients in need of such treatment in dosages that will provide optimal pharmaceutical efficacy. Doses may range from about 0.001 to 500 mg/kg (subject to tolerability limits) of body weight per day of Crystalline Form II. In one embodiment, the dosage is from about 0.01 to about 25 mg/kg of body weight per day of Crystalline Form II of verubecestat. In one embodiment, the dosage is from about 0.1 to about 1 mg/kg of body weight per day of Crystalline Form II. In one embodiment, the dosage is from about 0.24 to about 0.8 mg/kg of body weight per day of Crystalline Form II. In another embodiment, the quantity of active Crystalline Form II in a unit dose of preparation may be varied or adjusted from about 1 mg to about 100 mg, preferably from about 1 mg to about 50 mg, more preferably from about 1 mg to about 25 mg, according to the particular application. In another embodiment, the compositions may be provided in the form of tables containing 1.0 to 1000 milligrams of the active ingredient, such as 1, 5, 10, 12, 15, 20, 25, 40, 50, 60, 75, 100, 150, 200, 250, 300, 400, 500, 600, 750, 800, 900, and 1000 milligrams of the active ingredient for the adjustment of dosage according to the degree of Aβ lowering or other biological process desired.

In one embodiment, the dose is about 5 mg of Crystalline Form II of Verubecestat per dose. In another embodiment, the dose is about 10 mg of Crystalline Form II of Verubecestat per dose. In another embodiment, the dose is about 12 mg of Crystalline Form II of Verubecestat per dose. In another embodiment, the dose is about 40 mg of Crystalline Form II of Verubecestat per dose. In another embodiment, the dose is about 60 mg of Crystalline Form II of Verubecestat per dose. In another embodiment, the dose is about 100 mg of Crystalline Form II of Verubecestat per dose.

The Crystalline Form II of Verubecestat may be formulated for administration on, e.g., a regimen of from 1 to 4 times per day, including once or twice per day; in one embodiment once per day. In an alternative of each of the foregoing embodiments, the formulation is for once daily dosing.

In one embodiment, a dosage formulation comprises 12 mg of Crystalline Form II of verubecestat, lactose monohydrate, Povidone K29/32, croscarmellose sodium, and magnesium stearate.

In one embodiment, a dosage formulation comprises an intra granular layer comprising 12 mg of Crystalline Form II of verubecestat, lactose monohydrate, povidone, microcrystalline cellulose, and croscarmellose sodium, an extra granular layer comprising croscarmellose sodium and magnesium stearate, and optionally a film coating comprising Opadry II Blue coating material.

In one embodiment, a dosage formulation comprises 40 mg of Crystalline Form II of verubecestat, lactose monohydrate, povidone, microcrystalline cellulose, croscarmellose sodium, and magnesium stearate.

In one embodiment, a dosage formulation comprises an intra granular layer comprising 40 mg of Crystalline Form II of verubecestat, lactose monohydrate, microcrystalline cellulose, povidone, and croscarmellose sodium, an extra granular layer comprising croscarmellose sodium and magnesium stearate, and optionally a film coating comprising Opadry II Blue.

Example 1 provides a non-limiting example of a preparation of a coated tablet comprising 12 mg Crystalline Form II of verubecestat. Example 2 provides a non-limiting example of a preparation of a coated tablet comprising 40 mg Crystalline Form II of verubecestat.

Example 1

Purified water (700 g) was charged to a stainless steel container equipped with an agitator. Povidone (100 g) was added into the water while being stirred to form a granulation binder solution. Lactose Monohydrate (1185 g), Crystalline Form II of Verubecestat (150 g) and croscarmellose sodium (30 g) were charged directly into a fluidized bed granulator. This material was fluidized and the binder solution (600 g) was sprayed into the granulator to form granules. At the completion of the spraying process, the granules were dried and milled with a rotating impeller screening mill. The milled granules were charged into a diffusion-type mixer, croscarmellose sodium (45 g) was added into the mixer and blended for 75 revolutions. Magnesium stearate (15 g) was added into the mixer after passing through a stainless steel screen and blended for 45 revolutions. The blended material was compressed into tablet (cores) with target tablet weight of 120 mg using a rotary tablet press equipped with the product-specific tooling. The tablet cores were coated with Opadry® II film coating suspension.

Example 2

Purified water (700 g) was charged to a stainless steel container equipped with an agitator. Povidone (100 g) was added into the water while being stirred to form a granulation binder solution. Lactose Monohydrate (835 g), Crystalline Form II of Verubecestat (500 g) and croscarmellose sodium (30 g) were charged directly into a fluidized bed granulator. This material was fluidized and the binder solution (600 g) was sprayed into the granulator to form granules. At the completion of the spraying process, the granules were dried and milled with a rotating impeller screening mill. The milled granules were charged into a diffusion-type mixer, croscarmellose sodium (45 g) was added into the mixer and blended for 75 revolutions. Magnesium stearate (15 g) was added into the mixer after passing through a stainless steel screen and blended for 45 revolutions. The blended material was compressed into tablet (cores) with target tablet weight of 120 mg using a rotary tablet press equipped with the product-specific tooling. The tablet cores were coated with Opadry® II film coating suspension.

Methods of Use

As noted above, the scientific literature and recent clinical trials support the use of inhibitors of BACE-1 and BACE-2, including verubecestat, in a wide variety of indications, including Alzheimer's disease, including prodromal Alzheimer's disease. In each of these embodiments, reference to administration of the Crystalline Form II of Verubecestat refers to either administration of the neat chemical or in the form of a composition as described herein.

Thus, another embodiment provides a method of inhibiting β-secretase (BACE) comprising exposing a population of cells expressing β-secretase to Crystalline Form II of Verubecestat in an amount effective to inhibit β-secretase. In one such embodiment, said population of cells is in vivo. In another such embodiment, said population of cells is ex vivo. In another such embodiment, said population of cells is in vitro.

Additional embodiments in which the Crystalline Form II of Verubecestat may be useful include: a method of inhibiting β-secretase in a patient in need thereof, a method of inhibiting the formation of Aβ from APP in a patient in need thereof, and a method of inhibiting the formation of Aβ plaque and/or Aβ fibrils and/or Aβ oligomers and/or senile plaques and/or neurofibrillary tangles and/or inhibiting the deposition of amyloid protein (e.g., amyloid beta protein) in, on or around neurological tissue (e.g., the brain), in a patient in need thereof. Each such embodiment comprises administering the Crystalline Form II of Verubecestat in a therapeutically effective amount to inhibit said pathology or condition in said patient.

Additional embodiments in which the Crystalline Form II of Verubecestat may be useful include: a method of treating, preventing, and/or delaying the onset of one or more pathologies associated with Aβ and/or one or more symptoms of one or more pathologies associated with Aβ. Non-limiting examples of pathologies which may be associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $β_2$ microglobulins and complications arising therefrom in hemodialysis patients), scrapie, bovine spongiform encephalitis, and Creutzfeld-Jakob disease, said method(s) comprising administering to said patient in need thereof at least one Crystalline Form II in an amount effective to inhibit said pathology or pathologies.

Another embodiment in which the Crystalline Form II of Verubecestat may be useful includes a method of treating Alzheimer's disease, wherein said method comprises administering an effective amount of the Crystalline Form II of verubecestat, optionally in further combination with one or more additional therapeutic agents which may be effective to treat Alzheimer's disease or a disease or condition or one or more symptoms associated therewith, to a patient in need of treatment. In embodiments wherein additional therapeutic agents are administered, such agents may be administered sequentially or together, and formulated accordingly. Non-limiting examples of associated diseases or conditions, and non-limiting examples of suitable additional therapeutically active agents, are as described above.

Another embodiment in which the Crystalline Form II of Verubecestat may be useful includes a method of treating mild cognitive impairment ("MCI"), wherein said method comprises administering an effective amount of a Crystalline Form II of Verubecestat to a patient in need of treatment. In one such embodiment, treatment is commenced prior to the onset of symptoms.

Another embodiment in which the Crystalline Form II of Verubecestat may be useful includes a method of preventing, or alternatively of delaying the onset, of mild cognitive impairment or, in a related embodiment, of preventing or alternatively of delaying the onset of Alzheimer's disease. In such embodiments, treatment can be initiated at the earliest signs or symptoms (or sets of signs or symptoms) of Alzheimer's disease, e.g., as in prodromal patients, prior to the onset of symptoms, in some embodiments significantly before (e.g., from several months to several years before) the onset of symptoms to a patient at risk for developing MCI or Alzheimer's disease. Thus, such methods comprise administering, prior to the onset of symptoms or clinical or biological evidence of MCI or Alzheimer's disease (e.g., from several months to several years before, an effective and over a period of time and at a frequency of dose sufficient for the therapeutically effective degree of inhibition of the BACE enzyme over the period of treatment, an amount of a Crystalline Form II of Verubecestat to a patient in need of treatment.

Another embodiment in which the Crystalline Form II of Verubecestat may be useful includes a method of treating Down's syndrome, comprising administering an effective amount of a Crystalline Form II of Verubecestat to a patient in need of treatment.

In another embodiment, the invention provides methods of treating a disease or pathology, wherein said disease or pathology is Alzheimer's disease, olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, mild cognitive impairment, glaucoma, amyloidosis, type II diabetes, diabetes-associated amyloidogenesis, scrapie, bovine spongiform encephalitis, traumatic brain injury, or Creutzfeld-Jakob disease. Such methods comprise administering the Crystalline Form II of Verubecestat to a patient in need thereof in an amount effective to treat said disease or pathology.

In another embodiment, the invention provides for the use of the Crystalline Form II of Verubecestat for use as a medicament, or in medicine, or in therapy.

In another embodiment, the invention provides for use of the Crystalline Form II of Verubecestat for the manufacture of a medicament for the treatment of a disease or pathology, wherein said disease or pathology is Alzheimer's disease, olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, mild cognitive impairment, glaucoma, amyloidosis, type II diabetes, diabetes-associated amyloidogenesis, scrapie, bovine spongiform encephalitis, traumatic brain injury, or Creutzfeld-Jakob disease.

We claim:

1. A crystalline form of verubecestat characterized by a powder x-ray diffraction pattern with at least peaks at diffraction angles degrees 2 theta (+/−0.2°) of 10.94 and 14.98 in a powder x-ray diffraction obtained using Cu K alpha radiation.

2. The crystalline form of verubecestat according to claim 1, characterized by a powder x-ray diffraction pattern with at least peaks at diffraction angles degrees 2 theta (+/−0.2°) of 10.94, 14.53, 14.98, 16.23, 16.63, and 26.18.

3. The crystalline form of verubecestat according to claim 2, characterized by a powder x-ray diffraction pattern with at least peaks at diffraction angles degrees 2 theta (+/−0.2°) of 10.94, 14.53, 14.98, 16.23, 16.63, 17.77, 21.77, 23.24, and 26.18.

4. The crystalline form of verubecestat according to claim 3, characterized by a powder x-ray diffraction pattern with at least peaks at diffraction angles degrees 2 theta (+/−0.2°) of 10.94, 14.53, 14.98, 16.23, 16.63, 17.77, 20.84, 21.77, 23.24, 26.18, 30.88, and 33.39.

5. The crystalline form of verubecestat according to claim 4 characterized by substantially the same powder x-ray diffraction pattern as shown in FIG. 1.

6. The crystalline form of verubecestat of claim 1 exhibiting a melting endotherm with a peak temperature at 183.5° C. (+/−1° C.), measured by differential scanning calorimetry.

7. A crystalline form of verubecestat according to claim 6 exhibiting a melting endotherm with an extrapolated onset temperature of 181.7° C. (+/−1° C.) and a peak temperature at 183.5° C. (+/−1° C.), measured by differential scanning calorimetry.

8. The crystalline form of verubecestat according to claim 6 that exhibits a melting point substantially the same as shown in the differential scanning calorimetry scan of FIG. 2.

9. The crystalline form of verubecestat of claim 1 having a solid state $^{13}$C NMR spectrum exhibiting any two of the following peaks: 162.98, 160.46, 158.65, 156.39, 151.47, 145.63, 139.21, 133.72, 132.28, 125.50, 124.38, 122.10, 114.93, 57.11, 55.82, 29.22 and 25.66 ppm.

10. The crystalline form of verubecestat according to claim 9 having a solid state $^{13}$C NMR spectrum exhibiting any three of the following peaks: 162.98, 160.46, 158.65, 156.39, 151.47, 145.63, 139.21, 133.72, 132.28, 125.50, 124.38, 122.10, 114.93, 57.11, 55.82, 29.22 and 25.66 ppm.

11. The crystalline form of verubecestat according to claim 9 having a solid state $^{13}$C NMR spectrum exhibiting any four of the following peaks: 162.98, 160.46, 158.65, 156.39, 151.47, 145.63, 139.21, 133.72, 132.28, 125.50, 124.38, 122.10, 114.93, 57.11, 55.82, 29.22 and 25.66 ppm.

12. The crystalline form of verubecestat according to claim 9 having a solid state $^{13}$C NMR spectrum exhibiting any five of the following peaks: 162.98, 160.46, 158.65, 156.39, 151.47, 145.63, 139.21, 133.72, 132.28, 125.50, 124.38, 122.10, 114.93, 57.11, 55.82, 29.22 and 25.66 ppm.

13. The crystalline form of verubecestat according to claim 9 having a solid state $^{13}$C NMR spectrum exhibiting the following peaks: 162.98, 160.46, 158.65, 156.39, 151.47, 145.63, 139.21, 133.72, 132.28, 125.50, 124.38, 122.10, 114.93, 57.11, 55.82, 29.22 and 25.66 ppm.

14. The crystalline form of verubecestat according to claim 9 having a solid state $^{13}$C NMR substantially as shown in FIG. 4.

15. The crystalline form of verubecestat of claim 1 having an ORTEP representation as shown in FIG. 5.

16. The crystalline form of verubecestat according to claim 1 further characterized as exhibiting a peak temperature at 183.5° C. (+/−1° C.), measured by differential scanning calorimetry.

17. The crystalline form of verubecestat according to claim 16, further characterized as exhibiting a melting endotherm with an extrapolated onset temperature of 181.7° C. (+/−1° C.) and a peak temperature at 183.5° C. (+/−1° C.), measured by differential scanning calorimetry.

18. The crystalline form of verubecestat according to claim 1, further characterized by a solid state $^{13}$C NMR spectrum exhibiting any two of the following peaks: 162.98, 160.46, 158.65, 156.39, 151.47, 145.63, 139.21, 133.72, 132.28, 125.50, 124.38, 122.10, 114.93, 57.11, 55.82, 29.22 and 25.66 ppm.

19. The crystalline form of verubecestat according to claim 16, further characterized by a solid state $^{13}$C NMR spectrum exhibiting any two of the following peaks: 162.98, 160.46, 158.65, 156.39, 151.47, 145.63, 139.21, 133.72, 132.28, 125.50, 124.38, 122.10, 114.93, 57.11, 55.82, 29.22 and 25.66 ppm.

20. The crystalline form of verubecestat according to claim 17, further characterized by a solid state $^{13}$C NMR spectrum exhibiting any two of the following peaks: 162.98, 160.46, 158.65, 156.39, 151.47, 145.63, 139.21, 133.72, 132.28, 125.50, 124.38, 122.10, 114.93, 57.11, 55.82, 29.22 and 25.66 ppm.

21. The crystalline form of verubecestat according to claim 1, further having a ORTEP representation as shown in FIG. 5.

* * * * *